United States Patent
Fu et al.

(10) Patent No.: US 11,421,255 B2
(45) Date of Patent: Aug. 23, 2022

(54) METHOD FOR ENZYMATIC PREPARATION OF FLUDARABINE PHOSPHATE

(71) Applicant: Zhejiang Hisun Pharmaceutical Co., Ltd., Zhejiang (CN)

(72) Inventors: Dejin Fu, Zhejiang (CN); Yong Yang, Zhejiang (CN); Wei Yan, Zhenjiang (CN); Weijiang Wen, Zhejiang (CN); Xiande Gu, Zhejiang (CN); Hua Chen, Zhejiang (CN); Xiaojun Ma, Zhejiang (CN); Ling Zhang, Zhejiang (CN); Kaijun Wang, Zhejiang (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 1073 days.

(21) Appl. No.: 16/070,497

(22) PCT Filed: Jan. 20, 2016

(86) PCT No.: PCT/CN2016/071419
§ 371 (c)(1),
(2) Date: Jul. 16, 2018

(87) PCT Pub. No.: WO2017/124315
PCT Pub. Date: Jul. 27, 2017

(65) Prior Publication Data
US 2021/0198707 A1    Jul. 1, 2021

(51) Int. Cl.
*C12N 9/12*     (2006.01)
*C12P 19/32*    (2006.01)
*C12P 17/18*    (2006.01)

(52) U.S. Cl.
CPC .......... *C12P 17/182* (2013.01); *C12N 9/1205* (2013.01); *C12P 19/32* (2013.01); *C12Y 207/01028* (2013.01); *C12Y 207/02001* (2013.01)

(58) Field of Classification Search
CPC ............................. C12P 17/182; C12N 9/1205
See application file for complete search history.

(56) References Cited

U.S. PATENT DOCUMENTS

| | | | |
|---|---|---|---|
| 4,161,111 A | | 7/1979 | Hampl, Jr. |
| 4,164,444 A | * | 8/1979 | Whitesides .............. C12P 19/32 435/92 |
| 5,700,666 A | | 12/1997 | Hummel-Marquardt et al. |

FOREIGN PATENT DOCUMENTS

WO    WO 2007/144168    12/2007

OTHER PUBLICATIONS

Zou ("Efficient production of deoxynucleoside-5'-monophosphates using deoxynucleoside kinase coupled with a GTP-regeneration system" Applied Microbiology and Biotechnology, 2013, 97, 9389-9395) (Year: 2013).*
International Search Report for PCT/CN2016/071419 dated Sep. 28, 2016 (6 pages).
Barai V.N. et al., An Improved Method for the Enzymatic Transformation of Nucelosudes into 5'-Monophosphates:, Biotechnology Letters, vol. 26. No. 24, Dec. 31, 2004, pp. 1847-1850 (abstract).
Serra, I et al., "Immobilized *Drosophila melanogaster* Deoxyribunucleoside Kinase (DmdNK) as a High Performing Biocatalyst for the Synthesis of Purine Arabinonucleotides," Advanced Synthesis & Catalysis, vol. 365, Feb. 6, 2014, pp. 563-570 (abstract).
Serra, I et al., "Immobilized *Drosophila melanogaster* Deoxyribunucleoside Kinase (DmdNK) as a High Performing Biocatalyst for the Synthesis of Purine Arabinonucleotides," Advanced Synthesis & Catalysis, vol. 365, Feb. 6, 2014, pp. 563-570.

* cited by examiner

*Primary Examiner* — Robert J Yamasaki
*Assistant Examiner* — Charles Z Constantine
(74) *Attorney, Agent, or Firm* — Sheppard Mullin Richter & Hampton LLP

(57) ABSTRACT

A method for enzymatic preparation of fludarabine phosphate, comprising reaction of fludarabine with a high-energy phosphate compound under the action of deoxyribonucleic acid kinase. According to said method, acetate kinase and acetyl phosphate free acid or acetyl phosphate are also added. The technical problems present in the existing processes are successfully addressed by employing the enzymatic process to prepare the fludarabine phosphate. The usage of the high-energy phosphate compound is reduced by means of adding acetate kinase to recycle and regenerate a small amount of the high-energy phosphate compound, thereby reducing the generation of by-products having similar structures to the fludarabine phosphate, enhancing the operation convenience of purification steps in the industrial production of the fludarabine phosphate. The process is environment friendly, the reaction conditions are moderate, the cost is low, and the yield and the purity of the product obtained are high.

20 Claims, No Drawings

METHOD FOR ENZYMATIC PREPARATION OF FLUDARABINE PHOSPHATE

The present application is a national stage application of International Application PCT/CN2016/071419, filed Jan. 20, 2016, the contents of which are incorporated by reference in their entireties into the present disclosure.

TECHNICAL FIELD

The invention pertains to the technical field of medicine and particularly relates to a method for enzymatic preparation of fludarabine phosphate.

BACKGROUND OF ART

Fludarabine is a fluorinated nucleotide analogue of the antiviral drug vidarabine, which is mainly used for the treatment of chronic lymphocytic leukemia. Fludarabine is a purine compound that can be administered orally or intravenously. When fludarabine is phosphorylated, fludarabine phosphate will ionize at physiological pH and efficiently dissolve in blood. Accordingly, its levels in blood cells (including normal cells and cancer cells) will be significantly increased and it can inhibit tumor cells better. Its structural formula is as follow:

Fludarabine phosphate

Formula 1: Fludarabine phospate

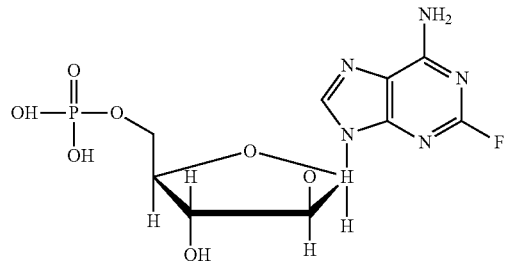

At present, the commercial fludarabine is in the form of its phosphate ester. In documents, the reported processes for preparing fludarabine phosphate from fludarabine are mainly divided into two types: one is the phosphorylation by a chemical method, and the other is the phosphorylation by an enzymatic method.

(A) Phosphorylation of Fludarabine by a Chemical Method

According to the research results of a large number of documents, the process of phosphorylation of fludarabine by a chemical method is mainly to carry out phosphorylation using phosphorus oxychloride as the reagent for phosphorylation as well as triethyl phosphate or trimethyl phosphate as the reaction solvent. The specific process route is as follows (Ref.

Reaction formula 2: The process of phosphorylation of fludarabine by a chemical method

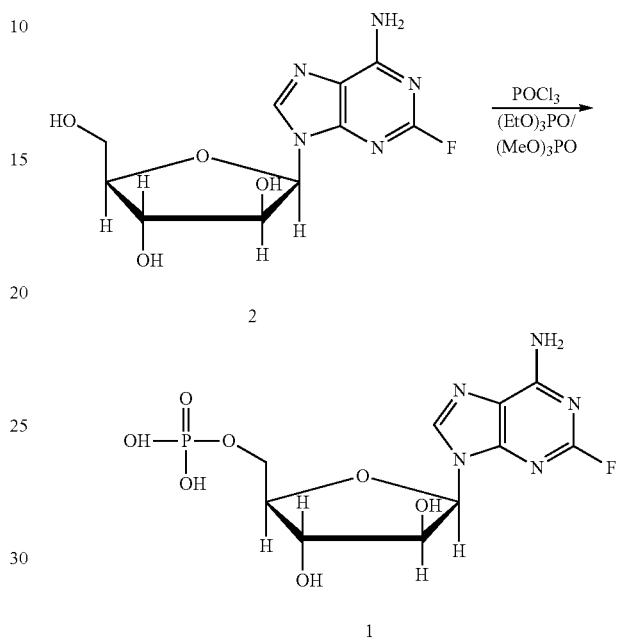

Process evaluation: this route is relatively mature and is the preferred process for phosphorylation by a chemical method, however, this route obviously has the following disadvantages: 1. highly toxic phosphorus oxychloride is used in this process, which brings greater pressure on EHS; 2 the synthesis process will produce impurities that are difficult to remove, the refining procedure is quite tedious; 3. the yield is low, which leads to a sharp increase in the cost as the price of fludarabine raw material is high.

(B) Phosphorylation of Fudarabine by an Enzymatic Method

In recent years, the process of phosphorylation by an enzymatic method has been explored. The highest concentration of fludarabine currently reported has reached 12 mM (about 3.42 g/L). The key steps of synthesis are as follows (Ref. Immobilized *Drosophila melanogaster* Deoxyribonucleoside Kinase (DmdNK) as a High Performing Biocatalyst for the Synthesis of Purine Arabinonucleotides, 2014):

Reaction formula 3: The process of phosphorylation of fludarabine by an enzymatic phosphorylation

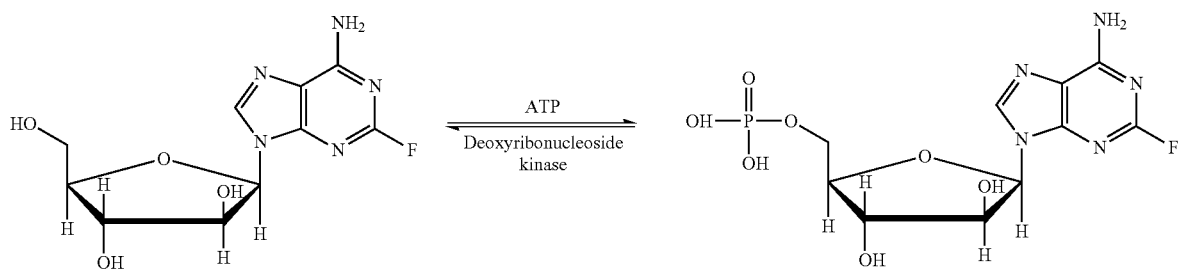

Process evaluation: The process route is relatively simple and the cost is low, but there are the following deficiencies: 1. the conversion of fludarabine is incomplete, leading to substrate residues, increasing the difficulty of purification; 2. lower substrate concentration; 3. a lot of ATP is needed in the reaction, the ADP generated by the reaction has a very similar structure to fludarabine phosphate, and it is difficult to separate and purify.

Another document has reported that deoxyvidarabine kinase (DddAK) in bacterial strain D. discoideum can be used for the synthesis of fludarabine phosphate from fludarabine (Ref. Dictyostelium discoideum Salvages Purine Deoxyribonucleosides by Highly Specific Bacterial-like Deoxyribonucleoside Kinases, 2007); Patent WO2007144168 has reported synthesis of fludarabine phosphate by catalyzing fludarabine with phosphate kinase, the mass yield of the crude product can reach 70% (Ref. WO2007144168, *Citrobacter amalonaticus, klebsiella sp., Klebsiella palnticalo, Serratia macescens, Enterobacter aerogenes, Enterobacter gergoviae*, kinases). An enzymatic process of fludarabine phosphate is also reported in WO9509244A1 (Ref. WO9509244A1). The above enzymatic processes all have the problems of low substrate concentration, difficult extraction and purification, and low product yield.

The above disclosed processes for preparing fludarabine phosphate all have obvious defects and do not meet the requirements of industrial production. Therefore, there is an urgent need for a production process that is easy to operate, safe, has low cost, has high product purity, and is environment-friendly.

SUMMARY OF THE INVENTION

The object of the present invention is to provide a method for enzymatic preparation of fludarabine phosphate, which is simple, safe, uses mild reaction conditions, has low production cost, high yield and purity, and is suitable for industrial production.

The present invention is implemented by the following technical solutions:

The present invention provides a method for enzymatic preparation of fludarabine phosphate, comprising a reaction of fludarabine with a high-energy phosphate compound under the action of deoxyribonucleic acid kinase, the method further comprises adding an acetate kinase and an acetyl phosphate free acid or an acetyl phosphate.

Preferably, the method includes the following steps:

(1) Adding a high-energy phosphate compound and an acetyl phosphate free acid or an acetyl phosphate to a fludarabine-containing reactant solution;

(2) Adding deoxyribonucleic acid kinase and acetate kinase to the solution obtained in step (1).

Preferably, the molar ratio of the acetyl phosphate free acid or acetyl phosphate to the fludarabine is (1.0-3.0):1; preferably, (1.5-2.5):1.

Deoxyribonucleic acid kinase, the abbreviation of which is dnk, the NCBI-Gene ID is 42273.

Acetate kinase, the abbreviation of which is ackA, the NCBI-Gene ID is 8181271.

Preferably, the high-energy phosphate compound is added in an amount of $0.001\text{-}0.003 \text{ mol·L}^{-1}$.

Preferably, the acetyl phosphate is acetyl phosphate dilithium.

Preferably, the high-energy phosphate compound is selected from the group consisting of the free acid of ATP, the free acid of ADP, the salt of ATP and the salt of ADP; more preferably, the high-energy phosphate compound is an ATP disodium salt.

The salts refer to the ones corresponding to the free acids.

The high-energy phosphate compound can also be selected from the group consisting of the free acid of GTP, the free acid of CTP, the salt of GTP and the salt of CTP.

Preferably, the deoxyribonucleic acid kinase and the acetate kinase are added in the form of whole cell, whole cell crushing liquid or immobilized enzyme.

The whole cell or whole cell crushing liquid is the one that express the deoxyribonucleic acid kinase and the acetate kinase. Preferably, the whole cell expressing the deoxyribonucleic acid kinase and the acetate kinase of the present invention is *Escherichia coli*.

Preferably, in the step (1), a soluble salt of $Mg^{2+}$ is added to the fludarabine-containing reactant solution; more preferably, the soluble salt of $Mg^{2+}$ is $MgCl_2 \cdot 6H_2O$ or $MgCl_2$.

Preferably, during the reaction, the pH is adjusted to 6.0-9.0; more preferably, the pH is adjusted to 7.5-8.5.

Preferably, in the step (1), a buffer substance is added to the fludarabine-containing reactant solution; more preferably, the buffer substance is ammonium acetate.

Preferably, the reaction temperature of the process of the present invention is 30-45° C.; more preferably, the reaction temperature is 37-40° C.

The method of the present invention is applicable not only to the preparation of fludarabine phosphate but also to the preparation of 5'-monophosphate nucleotide ester compounds.

A preferred technical solution of the present invention is shown in reaction formula 4:

Reaction formula 4: The process of enzymatic preparation of fludarabine phosphate according to the present invention

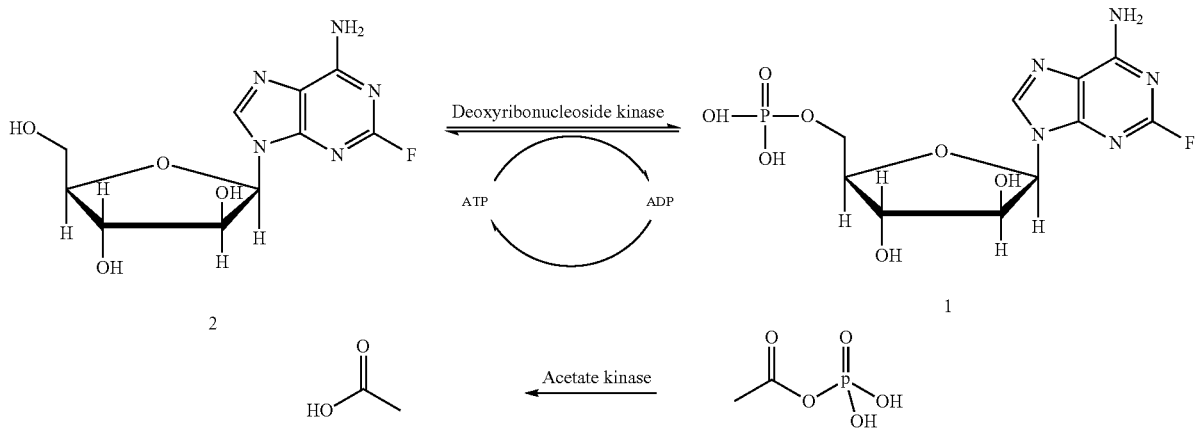

In reaction formula 4, deoxyribonucleoside kinase is deoxyribonucleic acid kinase; Acetate kinase is acetate kinase. The beneficial effects of the present invention lie in:

(1) The present invention prepares fludarabine phosphate by adopting a new enzymatic process and successfully solves the technical problems existing in the prior art. By adding acetate kinase and acetyl phosphate free acid or acetyl phosphate to recycle and regenerate a small amount of the high-energy phosphate compound, the usage of the high-energy phosphate compound is reduced, the use rate of the high-energy phosphate is increased, substrate concentration of fludarabine is increased, and the generation of by-products having similar structures to the fludarabine phosphate is also reduced, the operation convenience of purification steps in the industrial production of the fludarabine phosphate is greatly enhanced;

(2) The method of the present invention is environment-friendly, the reaction conditions are mild, the cost is low, and the yield and purity of the product obtained are high;

(3) The addition of soluble salts of $Mg^{2+}$ mayhelpthe deoxyribonucleic acid kinaseto play a catalytic role, and promotes enzyme activity.

EMBODIMENTS

The technical solutions and effects of the present invention will be further described below through specific examples. The following examples are only used to illustrate the content of the present invention, and are not intended to limit the protection scope of the present invention. The simple modifications of the present invention applying the concepts thereof are all within the protection scope of the present invention.

In the following examples, all materials are commercially available unless otherwise specified.

Fludarabine was purchased from Shanghai Zhao Wei Technology Development Co., Ltd., lot No.: FARA17A1;

Expression vector pET24a and *Escherichia coli E. coli* BL21 (DE3) were purchased from Invitrogen company;

Vector ESR-2 was purchased from Tianjin Nankai Hecheng Science & Technology Co., Ltd.

The construction of recombinant *Escherichia coli* expressing the deoxyribonucleic acid kinase and the acetate kinase: the deoxyribonucleic acid kinase (dnk, NCBI-Gene ID: 42273) gene and the acetate kinase (ackA, NCBI-Gene ID: 8181271) gene were directionally cloned onto the expression vector pET24a. The segment between the NdeI site and the BamHI site of the expression vector pET24a was replaced by the deoxyribonucleic acid kinase gene, and the segment between the BamHI site and the EcoRI site of the expression vector pET24a was replaced by the acetate kinase gene to obtain recombinant expression plasmids. The recombinant expression plasmids were genetic sequenced and identified. The results were consistent with expectations. The recombinant expression plasmids were then transferred into *Escherichia coli E. coli* BL21(DE3). The construction methods of the expression vectors and recombinant *Escherichia coli* referred to example No. 3 and example No. 5 in patent WO 00/39307 respectively. After identification by enzyme digestion, recombinant *Escherichia coli* were successfully constructed.

Obtaining of Wet Whole Cell:

Mediums were prepared, 600 ml of LB medium with a formula of: peptone 10 g/L, yeast extract 5 g/L, sodium chloride 10 g/L, pH=7.2; 30 L of TB medium with a formula of: peptone 12 g/L, yeast extraction 24 g/L, glycerin 5 g/L, monopotassium phosphate 2.13 g/L, dipotassium hydrogen phosphate trihydrate 16.43 g/L, pH=7.0-7.5;

Fermentation culture conditions: recombinant *Escherichia coli* expressing the deoxyribonucleic acid kinase and acetate kinase was inoculated into the LB liquid medium, was cultured overnight at 37° C. and 200 rpm, and then inoculated into TB medium at an inoculation amount of 2%, was cultured until OD=6-8 at 37° C. and 200 rpm, and then kanamycin with a final concentration of 50 mg/L was added into the TB medium, the culture was induced overnight at 25° C.;

After 24 h, OD=24 was measured, the fermentation was stopped, then centrifuged at 8000 rpm for 15 min, 1.2 kg of wet whole cell was collected, frozen at −20° C., preserved and stand by.

Obtaining of Immobilized Enzyme:

The recombinant *Escherichia coli* expressing the deoxyribonucleic acid kinase and the acetate kinase was immobilized on the vector of ESR-2 with the bacterial load ratio of 2:1, and the immobilization method refers to SCI of 2.4 in *A novel immobilization method for nuclease $P_1$ on macroporous absorbent resin with glutaraldehyde cross-linking and determination of its properties*, Process Biochemistry, 47(2012):665-670.

EXAMPLE 1

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.36 g of ATP disodium salt (0.003 mol·$L^{-1}$) and 10 g of fludarabine (about 0.035 mol) were added. 100 ml of tap water was added to the reaction system, and stirred it well, and the pH was adjusted to 8.0 with 6 mol·$L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.5-8.5 with NaOH. The reaction was completed after 5 hours, the conversion rate was >99.0%, and the protein was removed, concentrated hydrochloric acid was used to adjust the pH to 2.0 at room temperature, a large amount of white crystals precipitated, then the system was cooled down to 5-10° C., maintained for 1 hour. 9.8 g of fludarabine phosphate product was obtained by filtration. The final product content was 98.3%, the HPLC purity was 99.0%.

EXAMPLE 2

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.12 g of ATP disodium salt (0.001 mol·$L^{-1}$) and 10 g of fludarabine (about 0.035 mol) were added. 100 ml of tap water was added to the reaction system, and stirred it well, and the pH was adjusted to 8.0 with 6 mol·$L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.5-8.5 with NaOH. The reaction was completed after 7 hours, the conversion rate was 99.0%, and the protein was removed, concentrated hydrochloric acid was used to adjust the pH to 2.0 at room temperature, a large amount of white crystals precipitated, then the system was cooled down to 5-10° C., maintained for 1 hour. 9.7 g of fludarabine phosphate product was obtained by filtration. The final product content was 98.3%, the HPLC purity was 99.0%.

EXAMPLE 3

Into a four-necked flask of 250 mL, 0.77 g of ammonium acetate, 0.08 g of $MgCl_2 \cdot 6H_2O$, 7.98 g of acetyl phosphate dilithium (about 0.0525 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.5-8.5 with NaOH. The reaction was completed after 7 hours, the conversion rate was 99.0%, and the protein was removed, concentrated hydrochloric acid was used to adjust the pH to 2.0 at room temperature, a large amount of white crystals precipitated, then the system was cooled down to 5-10° C., maintained for 1 hour. 9.7 g of fludarabine phosphate product was obtained by filtration. The final product content was 98.5%, the HPLC purity was 99.1%.

EXAMPLE 4

Into a four-necked flask of 250 mL, 0.77 g of ammonium acetate, 0.08 g of $MgCl_2 \cdot 6H_2O$, 5.32 g of acetyl phosphate dilithium (about 0.035 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.5-8.5 with NaOH. The reaction was completed after 8 hours, the conversion rate was 90.2%, and the protein was removed, concentrated hydrochloric acid was used to adjust the pH to 2.0 at room temperature, a large amount of white crystals precipitated, then the system was cooled down to 5-10° C., maintained for 1 hour. 8.8 g of fludarabine phosphate product was obtained by filtration. The final product content was 96.0%, the HPLC purity was 97.6%.

EXAMPLE 5

Into a four-necked flask of 250 mL, 0.77 g of ammonium acetate, 0.08 g of $MgCl_2 \cdot 6H_2O$, 15.96 g of acetyl phosphate dilithium (about 0.105 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.5-8.5 with NaOH. The reaction was completed after 4 hours, the conversion rate was >99.0%, and the protein was removed, concentrated hydrochloric acid was used to adjust the pH to 2.0 at room temperature, a large amount of white crystals precipitated, then the system was cooled down to 5-10° C., maintained for 1 hour. 9.8 g of fludarabine phosphate product was obtained by filtration. The final product content was 96.2%, the HPLC purity was 99.0%.

EXAMPLE 6

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 6.5 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.0-7.5 with NaOH. The reaction was completed after 7 hours, the conversion rate was 97.3%, and the protein was removed, concentrated hydrochloric acid was used to adjust the pH to 2.0 at room temperature, a large amount of white crystals precipitated, then the system was cooled down to 5-10° C., maintained for 1 hour. 9.6 g of fludarabine phosphate product was obtained by filtration. The final product content was 98.0%, the HPLC purity was 98.5%.

EXAMPLE 7

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 9.0 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 8.5-9.0 with NaOH. The reaction was completed after 5 hours, the conversion rate was >99.0%, and the protein was removed, concentrated hydrochloric acid was used to adjust the pH to 2.0 at room temperature, a large amount of white crystals precipitated, then the system was cooled down to 5-10° C., maintained for 1 hour. 9.5 g of fludarabine phosphate product was obtained by filtration. The final product content was 98.7%, the HPLC purity was 98.8%.

EXAMPLE 8

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 10 $mol \cdot L^{-1}$ NaOH, the mixture was warmed up to 30° C. And then 10 g of wet whole cell containing the acetate kinase and the deoxyribonucleic acid kinase was weighed, dissolved in 100 ml of water, then was added to the reaction system, the temperature was maintained at 30-35° C., the pH during the reaction was controlled at 7.5-8.5 with NaOH. The reaction was completed after 7 hours, the conversion rate was 98.4%, and the protein was removed, concentrated hydrochloric acid was used to adjust the pH to 2.0 at room temperature, a large amount of white crystals precipitated, then the system was cooled down to 5-10° C., maintained for 1 hour. 9.64 g of fludarabine phosphate product was obtained by filtration. The final product content was 98.0%, the HPLC purity was 98.7%.

EXAMPLE 9

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 8 $mol \cdot L^{-1}$ NaOH, the mixture was warmed up to 45° C. And then 10 g of wet whole cell containing the acetate kinase and the deoxyribonucleic acid kinase was weighed, dissolved in 100 ml of water, then was added to the reaction system, the temperature was maintained at 40-45° C., the pH during the reaction was controlled at 7.5-8.5 with NaOH. The reaction was completed after 4 hours, the conversion rate was >99.0%, and the protein was removed, concentrated hydrochloric acid was used to adjust the pH to 2.0 at room temperature, a large amount of white crystals precipitated, then the system was cooled down to 5-10° C., maintained for 1 hour. 9.55 g of fludarabine phosphate product was obtained by filtration. The final product content was 97.8%, the HPLC purity was 98.1%.

EXAMPLE 10

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.28 g of ADP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.5-8.5 with NaOH. The reaction was completed after 5 hours, the conversion rate was >99.0%, and the protein was removed, concentrated hydrochloric acid was used to adjust the pH to 2.0 at room temperature, a large amount of white crystals precipitated, then the system was cooled down to 5-10° C., maintained for 1 hour. 9.76 g of fludarabine phosphate product was obtained by filtration. The final product content was 98.4%, the HPLC purity was 99.2%.

EXAMPLE 11

Into a four-necked flask of 250 mL, 0.77 g of ammonium acetate, 0.08 g of $MgCl_2 \cdot 6H_2O$, 15.2 g of acetyl phosphate diammonium salt (about 0.0875 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, then was added to the reaction system, the temperature was maintained at 37-40° C., the pH during the reaction was controlled at 7.5-8.5 with NaOH. The reaction was completed after 7 hours, the conversion rate was 98.0%, and the protein was removed, concentrated hydrochloric acid was used to adjust the pH to 2.0 at room temperature, a large amount of white crystals precipitated, then the system was cooled down to 5-10° C., maintained for 1 hour. 9.7 g of fludarabine phosphate product was obtained by filtration. The final product content was 98.1%, the HPLC purity was 99.0%.

EXAMPLE 12

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 6 $mol \cdot L^{-1}$ NaOH, the mixture was warmed up to 40° C. And then 10 g of wet whole cell containing the acetate kinase and the deoxyribonucleic acid kinase was weighed, dissolved in 100 ml of water, homogeneously breaked, then was added to the reaction system, the temperature was maintained at 37-40° C., the pH during the reaction was controlled at 7.5-8.5 with NaOH. The reaction was completed after 4 hours, the conversion rate was >99.0%, and the protein was removed, concentrated hydrochloric acid was used to adjust the pH to 2.0 at room temperature, a large amount of white crystals precipitated, then the system was cooled down to 5-10° C., maintained for 1 hour. 9.9 g of fludarabine phosphate product was obtained by filtration. The final product content was 98.7%, the HPLC purity was 99.6%.

EXAMPLE 13

Into a four-necked flask of 250 mL, 0.77 g of ammonium acetate, 0.08 g of $MgCl_2 \cdot 6H_2O$, 13.3 g of acetyl phosphate dilithium (about 0.0875 mol), 0.36 g of ATP disodium salt (0.003 $mol \cdot L^{-1}$) and 10 g of fludarabine (about 0.035 mol) were added. 100 ml of tap water was added to the reaction system, and stirred it well, and the pH was adjusted to 8.0 with 6 $mol \cdot L^{-1}$ NaOH, the mixture was warmed up to 40° C. And then 30 g of immobilized enzyme containing the acetate kinase and the deoxyribonucleic acid kinase was weighed and added to the reaction system, the temperature was maintained at 37-40° C., the pH during the reaction was controlled at 7.5-8.5 with NaOH. The reaction was completed after 8 hours, the conversion rate was 98.5%, and the protein was removed, concentrated hydrochloric acid was used to adjust the pH to 2.0 at room temperature, a large amount of white crystals precipitated, then the system was cooled down to 5-10° C., maintained for 1 hour. 9.1 g of fludarabine phosphate product was obtained by filtration. The final product content was 98.9%, the HPLC purity was 99.3%.

The invention claimed is:
1. A method for enzymatic preparation of fludarabine phosphate, comprising a reaction of fludarabine with a high-energy phosphate compound under the action of a deoxyribonucleic acid kinase, wherein the method further comprises adding an acetate kinase and an acetyl phosphate free acid or an acetyl phosphate.
2. The method according to claim 1, characterized in that the method comprises the following steps:

(1) adding a high-energy phosphate compound and an acetyl phosphate free acid or an acetyl phosphate to a fludarabine-containing reactant solution;

(2) adding a deoxyribonucleic acid kinase and an acetate kinase to the solution obtained in step (1).

3. The method according to claim 2, wherein the deoxyribonucleic acid kinase and the acetate kinase are added in the form of a whole cell, a whole cell crushing liquid, or an immobilized enzyme.

4. The method according to claim 3, wherein in the step (1), a soluble salt of $Mg^{2+}$ is added to the fludarabine-containing reactant solution.

5. The method according to claim 2, wherein the molar ratio of the acetyl phosphate free acid or acetyl phosphate to the fludarabine is (1.0-3.0):1.

6. The method according to claim 2, wherein the high-energy phosphate compound is added in an amount of 0.001-0.003 mol·$L^{-1}$.

7. The method according to claim 2, wherein the acetyl phosphate is acetyl phosphate dilithium.

8. The method according to claim 2, wherein the high-energy phosphate compound is selected from the group consisting of the free acid of ATP, the free acid of ADP, the salt of ATP and the salt of ADP.

9. The method according to claim 2, wherein the deoxyribonucleic acid kinase and the acetate kinase are added in the form of a whole cell, a whole cell crushing liquid, or an immobilized enzyme.

10. The method according to claim 2, wherein during the reaction, the pH is adjusted to 6.0-9.0.

11. The method according to claim 2, wherein the reaction temperature is 30-45° C.

12. The method according to claim 1, wherein the molar ratio of the acetyl phosphate free acid or acetyl phosphate to the fludarabine is (1.0-3.0):1.

13. The method according to claim 12, wherein the acetyl phosphate is acetyl phosphate dilithium.

14. The method according to claim 12, wherein the high-energy phosphate compound is selected from the group consisting of the free acid of ATP, the free acid of ADP, the salt of ATP and the salt of ADP.

15. The method according to claim 1, wherein the high-energy phosphate compound is added in an amount of 0.001-0.003 mol·$L^{-1}$.

16. The method according to claim 15, wherein the acetyl phosphate is acetyl phosphate dilithium.

17. The method according to claim 1, wherein the acetyl phosphate is acetyl phosphate dilithium.

18. The method according to claim 1, wherein the high-energy phosphate compound is selected from the group consisting of the free acid of ATP, the free acid of ADP, the salt of ATP and the salt of ADP.

19. The method according to claim 1, wherein during the reaction, the pH is adjusted to 6.0-9.0.

20. The method according to claim 1, wherein the reaction temperature is 30-45° C.

* * * * *